(12) United States Patent
Hernandez-Garcia et al.

(10) Patent No.: US 9,744,373 B2
(45) Date of Patent: Aug. 29, 2017

(54) MULTI-COIL TRANSCRANIAL MAGNETIC STIMULATION

(75) Inventors: Luis Hernandez-Garcia, Ann Arbor, MI (US); Anthony Grbic, Ann Arbor, MI (US); Eric Michielssen, Ann Arbor, MI (US); Luis Gomez, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 671 days.

(21) Appl. No.: 14/130,707

(22) PCT Filed: Jul. 5, 2012

(86) PCT No.: PCT/US2012/045499
§ 371 (c)(1),
(2), (4) Date: Aug. 27, 2014

(87) PCT Pub. No.: WO2013/006670
PCT Pub. Date: Jan. 10, 2013

(65) Prior Publication Data
US 2014/0364679 A1 Dec. 11, 2014

Related U.S. Application Data

(60) Provisional application No. 61/504,605, filed on Jul. 5, 2011.

(51) Int. Cl.
*A61N 2/02* (2006.01)
*A61N 1/40* (2006.01)
*A61N 2/00* (2006.01)

(52) U.S. Cl.
CPC .............. *A61N 2/02* (2013.01); *A61N 1/40* (2013.01); *A61N 2/006* (2013.01)

(58) Field of Classification Search
CPC .... G01R 33/385; G01R 33/3806; A61B 5/055
See application file for complete search history.

(56) References Cited

U.S. PATENT DOCUMENTS

| 5,738,625 A | 4/1998 | Gluck |
| 6,179,771 B1 | 1/2001 | Mueller |

(Continued)

OTHER PUBLICATIONS

International Search Report and Written Opinion of the ISA, ISA/KR, mailed Jan. 23, 2013.

*Primary Examiner* — Christine H Matthews
(74) *Attorney, Agent, or Firm* — Harness, Dickey & Pierce, P.L.C.

(57) ABSTRACT

An improved apparatus is provided for transcranial magnetic stimulation in a brain of a subject. The apparatus is comprised of: a plurality of coils electrically connected in series to each other; and a single source of current electrically coupled to one of the plurality of coils. Each coil may include one or more windings of similar dimensions although the size of the windings varies between coils. Each of the coils is further dimensioned to stimulate brain tissue at a given distance while minimizing volume of the brain tissue excited by the magnetic field. During operation, the current source injects time varying current into the coils to create a magnetic field which in turn induces electric fields and eddy-currents inside the brain tissue of the subject.

9 Claims, 12 Drawing Sheets

(56) References Cited

U.S. PATENT DOCUMENTS

| | | | |
|---|---|---|---|
| 6,425,852 B1 | 7/2002 | Epstein et al. | |
| 2005/0046532 A1* | 3/2005 | Dodd | G01R 33/385 335/299 |
| 2005/0057249 A1 | 3/2005 | Dale et al. | |
| 2006/0287566 A1 | 12/2006 | Zangen et al. | |
| 2011/0133739 A1* | 6/2011 | Tieng | G01R 33/381 324/318 |

* cited by examiner

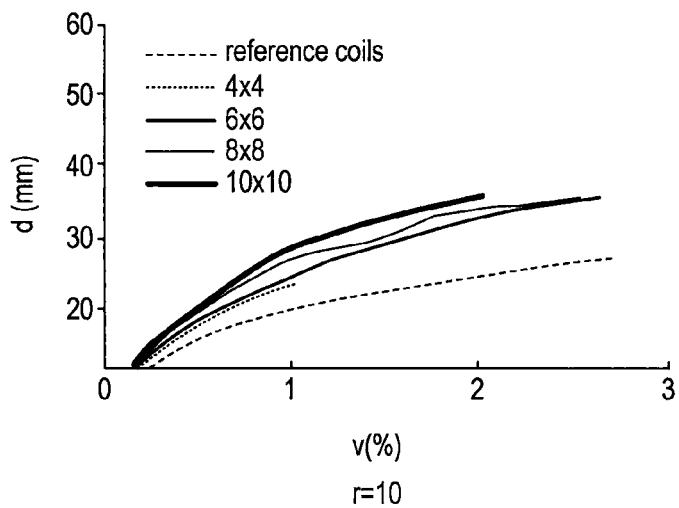
FIG. 6D
FIG. 6E
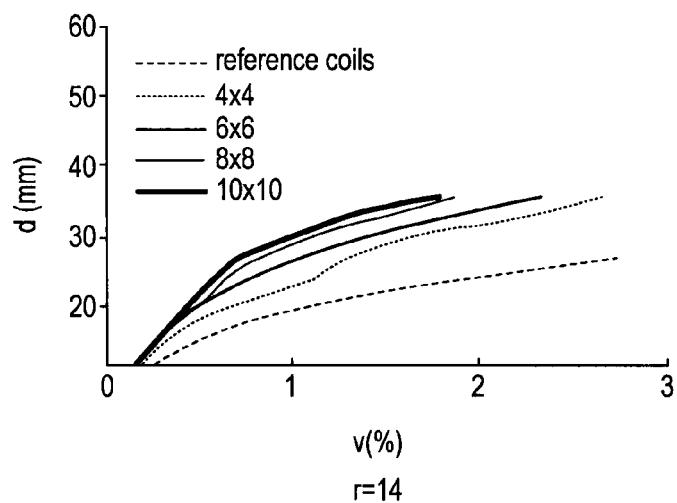
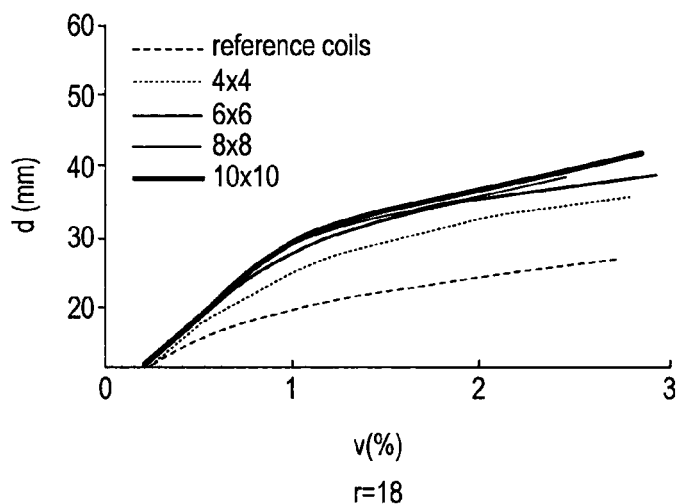
FIG. 6F

48x48mm sized array

64x64mm sized array

80x80mm sized array

96x96mm sized array

120x120mm sized array

160x160mm sized array

MULTI-COIL TRANSCRANIAL MAGNETIC STIMULATION

CROSS-REFERENCE TO RELATED APPLICATIONS

This application is a 371 U.S. national phase application based on PCT/US2012/045499, filed Jul. 5, 2012 and published in English on Jan. 10, 2013, which claims the benefit of U.S. Provisional Application No. 61/504,605, filed Jul. 5, 2011. The entire disclosures of the above applications are incorporated herein by reference.

GOVERNMENT CLAUSE

This invention was made with government support under grant no. NS058691 awarded by the National Institutes of Health. The Government has certain rights in the invention.

FIELD

The present disclosure relates generally to transcranial magnetic stimulation.

BACKGROUND

Transcranial magnetic stimulation (TMS) is a noninvasive brain stimulation technique holding significant promise as a tool for cognitive neuroscience, and for psychiatric treatment of neurological disorders. In TMS, one or more coils carrying time varying current located near the scalp generate magnetic fields inside the head that in turn induce electric fields and eddy-currents inside conductive brain tissue. Whenever a nerve fiber is aligned with the induced electric field, a current is produced in the axon, which in turn depolarizes its membrane. A large induced electric field is essential for neuronal stimulation. TMS coils generate substantial unwanted stimulation outside the desired region, and stimulate large regions of tissue limited to areas near the surface of the brain because the electric field becomes diffuse and decays rapidly with increasing distance from the coil.

Historically, numerous attempts have been made to design TMS coils capable of delivering more focused electric fields deep into the brain. For example, many single coil topologies have been explored. Further improvements are needed. Accordingly, this disclosure introduces a multi-channel coil array design that stimulates a specific target region while minimizing stimulation elsewhere.

This section provides background information related to the present disclosure which is not necessarily prior art.

SUMMARY

An improved apparatus is presented for transcranial magnetic stimulation in a brain of a subject. The apparatus is comprised of: a plurality of coils electrically connected in series to each other; and a single source of current electrically coupled to one of the plurality of coils. Each coil may include one or more windings of similar dimensions although the size of the windings varies between coils. Each of the coils is further dimensioned to stimulate brain tissue at a given distance while minimizing volume of the brain tissue excited by the magnetic field. During operation, the current source injects time varying current into the coils to create a magnetic field which in turn induces electric fields and eddy-currents inside the brain tissue of the subject.

In another aspect of this disclosure, a computer-assisted method is presented for constructing an apparatus for transcranial magnetic stimulation. The method includes: modeling an apparatus for transcranial magnetic stimulation as an array of coils that induce an electric field at a given distance, where each coil is configured to receive a respective driving current; formulating a set of designs for the apparatus, such that each design is represented by a vector and each element of the vector stores a value of current driving a respective coil in the array of coils; iteratively applying a genetic algorithm to the set of designs to yield an optimal design for the apparatus; and constructing the apparatus for transcranial magnetic stimulation based on the optimal design for the apparatus.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

FIGS. 6A-6F are graphs illustrating the tradeoffs of coil arrays as a function of number of elements;

Figure 1:
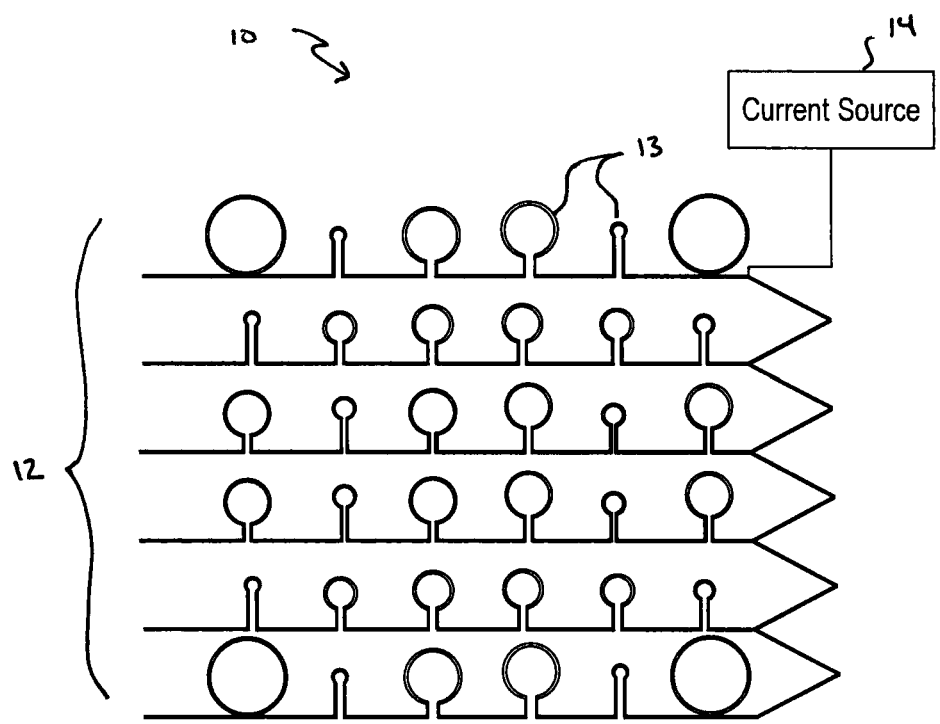
FIG. 1 is a diagram of an exemplary apparatus implementing transcranial magnetic stimulation (TMS) in a brain of a subject.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

FIG. 1 depicts an exemplary apparatus 10 implementing transcranial magnetic stimulation in a brain of a subject. The apparatus 10 is comprised generally of: a plurality of conductive coils 12 and a single current source 14. The coils 12 are electrically connected in series to each other. Each coil 13 may include one or more windings of similar dimensions although the size of the windings varies between coils. Each of the coils is dimensioned stimulate brain tissue at a given distance while minimizing volume of the brain tissue excited by the magnetic field as will be further described below. In an exemplary embodiment, the coils are arrange in an n by n square array as shown in FIG. 1, where n is an integer greater than one. Other planar arrangements for the coils 12 are also contemplated by this disclosure.

During operation, the coils 12 carry time varying current injected into the coils 12 by the single current source 14. The coils generate a magnetic field which in turn induces electric fields and eddy-currents inside the brain tissue of the subject. The effects of the fields generated by the coils 12 on the brain are complex, and highly dependent on the magnitude and timing of the TMS pulse. Although small fields can potentially cause neurons to depolarize, for the purposes of this disclosure, assume that most neuronal activity only occurs when the electric field magnitude exceeds 150V/m. To determine the stimulated region, the electric fields generated during TMS inside the head are found and then the region that is above 150V/m is extracted. Two exemplary models used for the head of the subject may include a concentric spherical model and one obtained from in vivo MRI imaging data.

A quasi-magneto static method may be used to find the electric fields of each TMS coil because typical TMS pulses generate fields in the 1 kHz-10 KHz frequency range. First, solve for the magnetic field using biot-savart law provide below as equation (1). Previously obtained magnetic fields are then used to calculate electric fields and eddy currents inside the inhomogeneous conductive region by enforcing equations (2) and (3) set forth below. In equation (3), displacement currents are neglected as they are much smaller than the conduction currents generated inside the brain.

$$B(r) = \frac{\mu_0}{4\pi} \int J(r') \times \frac{r-r'}{|r-r'|^3} dr', \quad (1)$$

$$\oint_C E(r) \cdot dl = -\frac{d}{dt} \int\int_S B(r) \cdot ds, \quad (2)$$

$$\int\int_{S_c} \sigma(r)E(r) \cdot ds = 0. \quad (3)$$

In the above equations, J(r) is the coil current, E(r) is the total electric field, B(r) is the total magnetic flux produced by the TMS coil, μ(r) and δ(r) are the permeability and conductivity at r. The time derivative in equation (2) is assumed to equate to a linear scalar factor multiplying the magnetic field derived from the time derivative of the coil current. In equation (1), r' is the location of the coil current elements and $\mu_0$ is the permeability of free space. In equation (2), C is an arbitrary contour enclosing a surface S. In equation (3), $S_c$ is an arbitrary closed surface. Equations 1-3 may be solved using the method described by Cerri et al. in "An Accurate 3-D Model for Magnetic Stimulation of the Brain Cortex" J Med Eng Technology January-February 1995. Briefly, a quadrature rule may be used to calculate the magnetic field through the domain. The electric field is then determined by splitting the brain into homogenous conductive cubic cells. To calculate the right hand side, equation (2) is applied on cell faces and the magnetic fields are used from the previous step. Equation 3 is applied on a cubic volume centered about each node.

Consider two different coil designs, denoted coil A and coil B. Suppose, we test each coil to see how well they target frontal lobe and the parietal lobe of the cortex. Coil A is found to be better for targeting the frontal lobe, and Coil B is better for targeting the parietal lobe. A TMS researcher interested in exciting the frontal lobe would say that Coil A is better than B, while one interested in the parietal lobe would find Coil B superior to A. One cannot say that one coil is superior to the other. Thus, a set of coil designs cannot be ranked because the best design is dependent on the goals of the TMS researcher. The set of coil designs would be considered 'Pareto optimal' as they each possess the quality that no design is better in all situations than it. In a Pareto analysis, the aim is to find the set of designs—known as the Pareto front—that best target each sub-region of the head.

To rank each coil in terms of its effectiveness at stimulating a certain target region of the brain, consider the electric field that it induces inside the head. Two parameters are extracted by considering the stimulated region of the brain (i.e., the region of the head with electric fields, for example, above 150V/m). The first parameter is a Boolean variable, denoted P, which indicated whether the target was successfully stimulated and defined as in (4).

$$p = \begin{cases} \text{true} & \|E(\text{target})\|_2 \geq 150\frac{V}{m} \\ \text{false} & \|E(\text{target})\|_2 < 150\frac{V}{m} \end{cases}, \quad (4)$$

The other parameter measures the volumetric extent excitation; it is volume of the stimulated region, which may be called the 'stimulated volume' (v) and is defined as in (5).

$$v = \int\int\int_{r \in \{brain \cap \|E(r)\|_2 \geq 150\frac{V}{m}\}} dr, \quad (5)$$

A coil is considered superior to another if it is able to stimulate the target while stimulating less total volume; in other words, the aim is to minimize v given p=true.

The magnitude of the electric field is directly proportional to the magnitude of the driving coil currents and can be easily changed (e.g. by changing amplifier parameters). Thus, for each design, the maximum field is normalized inside the head from 150V/m to 450V/m in steps of 10V/m and record v and p each time; however, only considering the coil's minimum v such that p=true when comparing it to other coils. In an exemplary embodiment, the field inside the head is not allowed to exceed a predefined threshold (e.g., 450V/m) because of safety standards. If a coil is not able to excite the target under the above conditions it is given the worse possible ranking.

Given a set of TMS coil designs, a Pareto front would contain the minimum attainable v's for each different target region. In other words, the front contains target region of the brain versus v tradeoffs. Once constructed, the front can be used to determine the optimal design from the set for a given TMS application.

Figure 2:
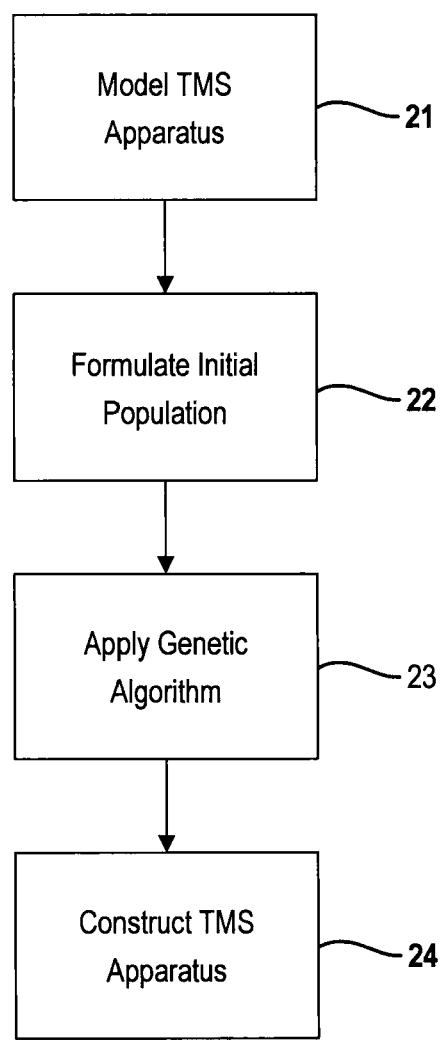
FIG. 2 is a flowchart depicting an exemplary computer-assisted method for determining an optimal coil design for a TMS apparatus.

FIG. 2 depicts an exemplary computer-assisted method 20 for determining an optimal coil design for an apparatus 10 implementing transcranial magnetic stimulation. The apparatus for transcranial magnetic stimulation is first modeled at 21 as an array of coils, such that each coil is configured to receive an individual driving current.

Next, a set of coil designs is selected at 22 for evaluation. In an exemplary embodiment, each design is represented by a vector, such that each element corresponds to a designated coil in the array of coils and stores a value of current driving the corresponding coil in the array of coils. Since each individual driving current can take an arbitrary value, the design space is large. In the exemplary embodiment, a single-objective genetic algorithm is applied iteratively at 23 to the set of designs, thereby yielding an optimal design for the apparatus. It is envisioned that other types of optimization techniques may be used to evaluate the set of coil designs.

Briefly, genetic algorithms create solutions to optimization problems using techniques inspired by natural evolution. In genetic algorithms, an initial population of designs is used to create successive populations with on-average improved designs until the algorithm converges and yields an optimal design for the apparatus. Although genetic algorithms can be implemented in different ways and using a wide range of operators, an exemplary implementation is further described below.

In an exemplary implementation, the genetic algorithm seeks the minimum of a cost function whose value is determined by the design parameters. To do this, each coil in a given design is assigned an integer valued relative current between −999 and 999 and encoded into a vector of length $N_{coils}$, where the vector is commonly referred to as a chromosome and denoted herein as x. The initial population of $N_{pop}$ designs is chosen by randomly selecting chromosomes uniformly from the design space.

All of the coil designs of each population are evaluated according to the cost function, which determines the quality of the design. First, the designs are ranked in increasing cost function value. An Elite operator may be applied to ensure that top $N_{elite}$ designs automatically get promoted to the next generation. The remaining $N_{pop}-N_{elite}$ individuals of the next generation are derived from slightly modified versions of individuals in the current population; these individuals are known as parents and are chosen by the selection operator. In the exemplary implementation, a roulette-wheel selection procedure is used to select parents. In roulette-wheel selection, a discrete probability function is created by assigning each individual in the population probability of becoming a parent proportional to the individual's cost function value; equation (6) is used to determine the probability value of each individual. Then, parents are chosen randomly by using the following distribution function:

$$E(i) = \frac{\frac{1}{\sqrt{r_i}}}{\sum_i \frac{1}{\sqrt{r_i}}} \quad (6)$$

In equation (6), $r_i$ is the rank of the i-th individual and E(i) is the probability of the i-th individual. Sections of the wheel are chosen at random to select parents until enough parents to create a generation $N_{pop}$ have been chosen. A crossover function creates $N_{crossover}$ children each from a weighted average of two parents by using a number α chosen from a uniform distribution having values between 0 and 1. Each child is created using equation (7), where $x_c$ is the child, and $x_{p1}$ and $x_{p2}$ are the parents. Note in equation (7) only the integer part of each number in $x_c$ is stored and the rest is truncated.

$$x_c = (1-\alpha)x_{p1} + \alpha x_{p2} \quad (7)$$

The Mutation operator creates $N_{mutation}$ children by first creating a vector, denoted ε, for each mutation child of length $N_{coils}$ of random numbers each chosen from a Gaussian distribution with variance (8) and then adding it to the parent as in (9). In equation (8), S and R are parameters called shrink and range, respectively, g is the generation number, $N_g$ is the number of generations.

$$\sigma = \left(1 - S\frac{g}{N_g}\right)R \quad (8)$$

$$x_c = x_{p1} + \varepsilon \quad (9)$$

The cost function value is obtained by considering the electric fields induced inside the brain by each set of driving currents. Evaluating the field each time using the method described above would be prohibitive since it requires a lot of computation. Instead, to evaluate the electric field rapidly, the electric field generated by each coil is pre-computed when loaded with a unit time-derivative current, called a lead field. Then, the electric field due to the ith coil can be expressed as the product of the time derivative of the coil current $I_i$ and its lead field $L_i(r)$. The total field E(r) generated by the array is the superposition of all the individual coil fields as in (10).

$$E(r) = \sum_{i=1}^{N_c} \frac{\partial I_i}{\partial t} L_i(r) \quad (10)$$

The genetic algorithm solves for optimal relative driving currents. Once we calculate the total electric field, the total electric field is renormalize by making the minimum field inside the target volume 150V/m thus ensuring p is true and v is minimum. The value of the cost function (11) is v or equal to the head volume if the resultant peak field inside the head from the above renormalization is above 450V/m, which corresponds to the worst possible design.

$$\cos t = \begin{cases} \min(v) & \max_{r \in \{head\}} |E(r)| \leq 450 \text{ V/m} \\ \int\int\int_{r \in \{head\}} dr & \max_{r \in \{head\}} |E(r)| > 450 \text{ V/m} \end{cases} \quad (11)$$

The algorithm stops when the minimum cost of a population does not decrease for predefined number of (e.g., 30) consecutive generations. To prevent false convergence, the genetic algorithm may be run to include the best designs from the previous run in the initial population.

Finally, an apparatus for transcranial magnetic stimulation can be constructed at 24 from the optimal design. Rather than driving coils individually, coils in the apparatus are driven by a single current source. Thus, the multi-channel array of coils needs to be converted into a single channel array. To do so, each coil in the array of coils is configured to mimic the magnetic dipole moment of a corresponding coil in the optimal design for the apparatus. In one implementation, the coils are configured by stacking multiple coils and adding inner coils of fractional area to effectively mimic the magnetic dipole moment of each coil. Each pareto optimal design consist of $N_{coils}$ coils each having an area $A_i$ and a total current $I_i$, I denotes the index of the coil. It is envisioned that the magnetic dipole moment can be mimicked by leveraging one current source that provides a total current I. First, each single winding coil of the array is replaced with an identical coil but each with multiple windings where the number of windings $N_i$ is determined by (12). The remainder flux is generated by adding an inner loop $r_{i,inner}$ with radius determined by (13). The polarity of each coil is determined by the sign of the original driving current value.

$$N_{i,1} = \text{floor}\left(\left|\frac{I_i}{I}\right|\right), \quad (12)$$

$$r_{i,inner} = \sqrt{\frac{|I_i - N_iI|A_i}{\pi I}} \quad (13)$$

Figure 3:
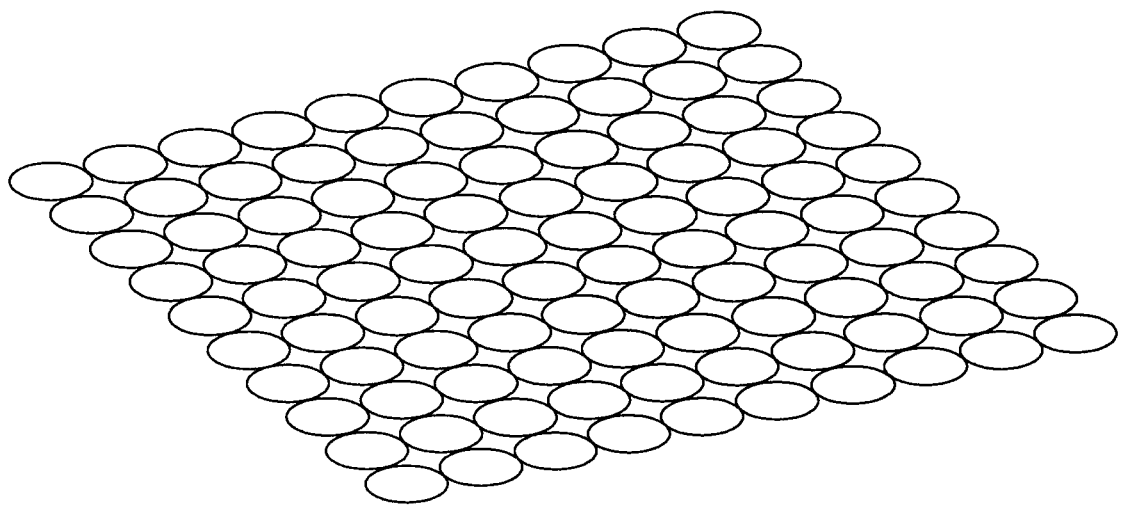
FIG. 3 is a perspective view of an exemplary planar coil array for use in the TMS apparatus.

Test results support the approach set forth above. Consider a planar square array consisting of non-uniformly fed identical circular coils each with radius (r) (chosen to be 4, 6, 8, 10, 14, 18 mm) placed in a square lattice and centered 1 cm above the head as shown in FIG. 3. The localization and efficiency of the arrays were compared with a variety of reference coils. For example, the 'figure-8' coil geometry, which consists of two adjacent circular filamentary current sources each with a current of equal magnitude, radius ($r_{coil}$) (which we allow to vary between 15 mm to 30 mm), and an angle theta (θ) (which we allow to vary between 0 and 180), between them was modeled. The commercially available BC-70 coil composed of two bent arithmetic spiral coils with 10 turns and inner and outer radii of 12 mm and 54 mm respectively was modeled. Ten H-coils were also designed and tested, which are designed to conform to the spherical head and have a target region directly under the scalp.

Figure 4A:
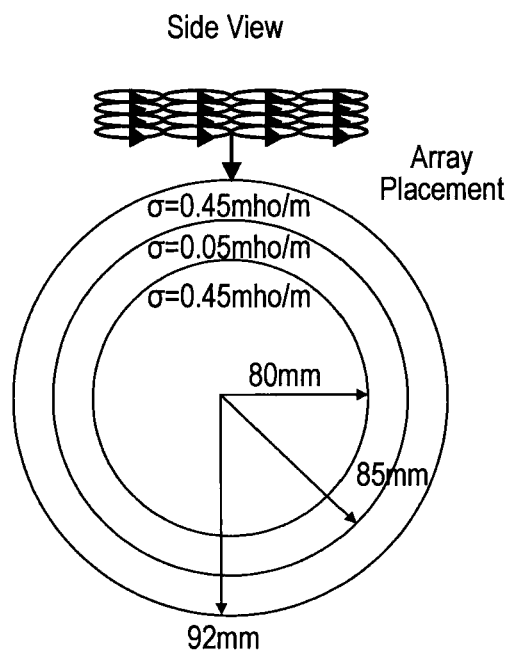
FIGS. 4A and 4B are a side view and top view depicting placement of a TMS apparatus having planar coil array in relation to a 3-sphere conductive head model, respectively.
Figure 4B:
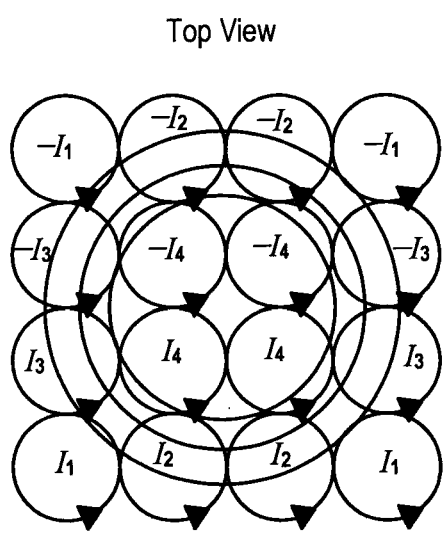
Figure 5A:
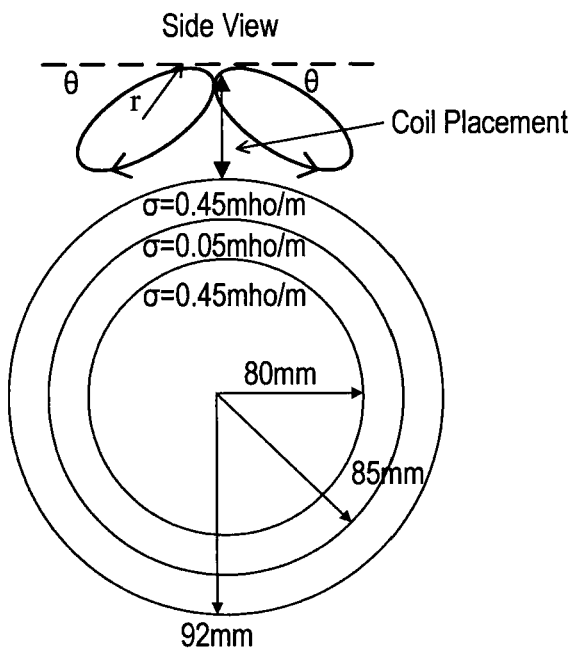
FIGS. 5A and 5B are a side view and top view depicting placement of a TMS apparatus having a reference coil in relation to a 3-sphere conductive head model, respectively.
Figure 5B:
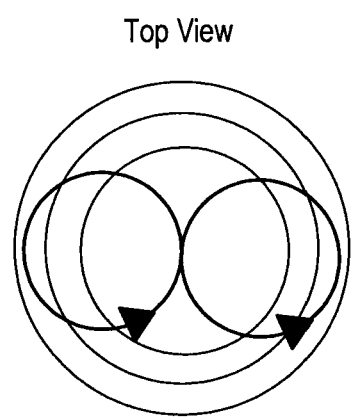

The electric field generated by each of the different TMS systems was analyzed inside a 3-sphere conductive head model, which is commonly used to benchmark TMS coils, as shown in FIGS. 4A and 4B. The goal is to target each individual voxel inside the head. Because of the axial symmetry of the conductivity model this is equivalent to targeting each voxel confined to a vertically oriented line centered about the axis of the spherical head. The study included single voxel targets at each depth d and the Pareto front describing optimal d vs. v tradeoffs. The array was placed 1 cm above the head centered above the vertical line (as shown in FIG. 4A) and because of the axial symmetry of the setup assume two symmetries in the driving currents and thus all of the array driving currents are determined from a one quadrant of currents. Once the driving currents are chosen for one quadrant of the array, the other three quadrants are determined by: i) choosing the driving currents of one of the adjacent quadrants to be an exact mirror of the chosen quadrant driving currents, ii) driving the other two quadrants by currents corresponding to a negated mirror image of the initial two. Each reference coil is characterized by placing it centered above the vertical line (see FIG. 4B) and recording d vs. v tradeoffs, by varying the vertical distance between the head and the coil between 10 mm to 31 mm in steps of 3 mm.

Figure 6A:
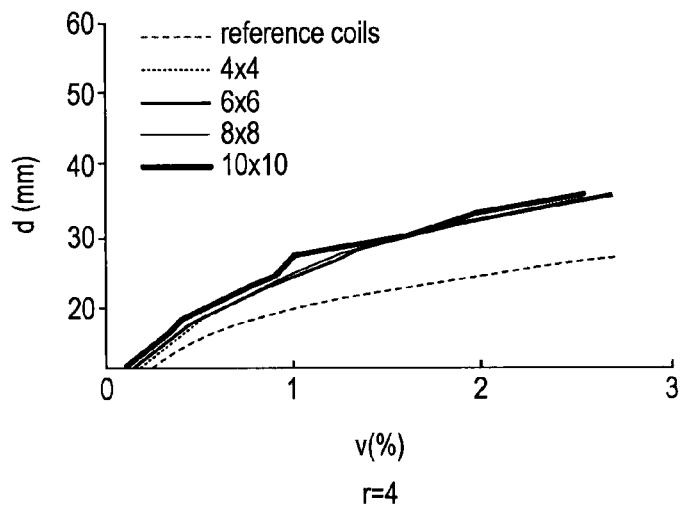
Figure 6B:
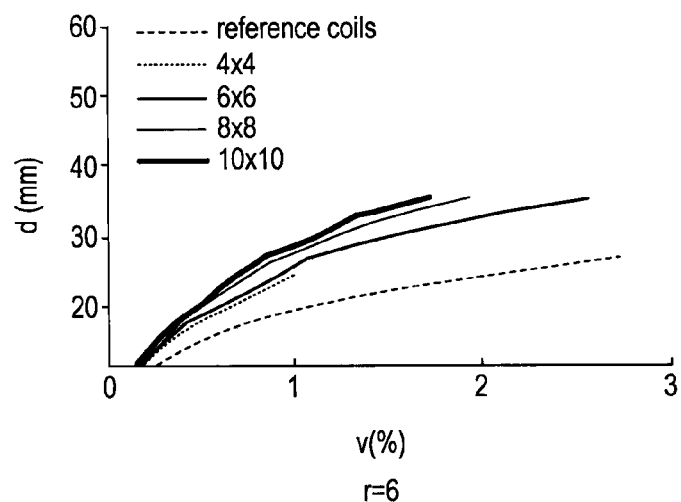
Figure 6C:
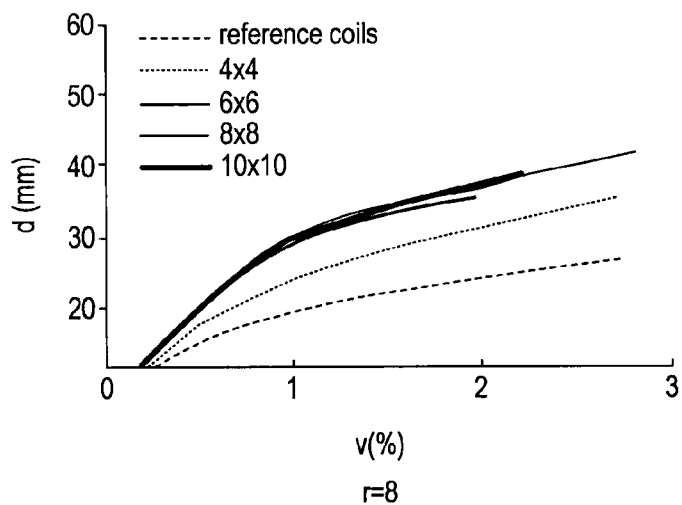
Figure 7A:
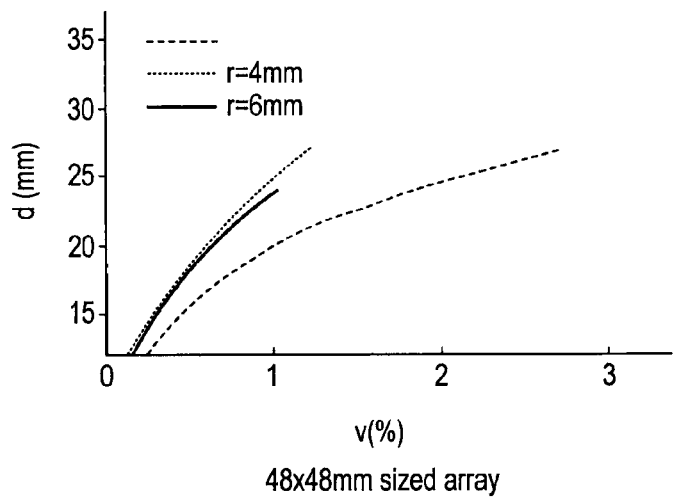
FIGS. 7A-7F are graphs illustrating the tradeoffs of coil arrays as a function of the size of the individual coils.
Figure 7B:
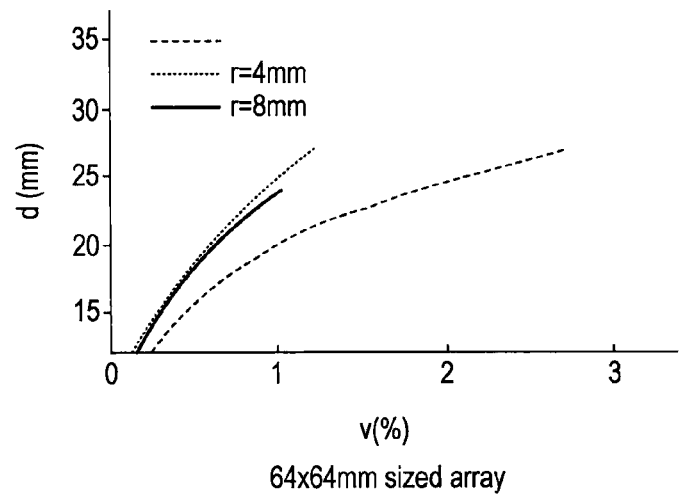
Figure 7C:
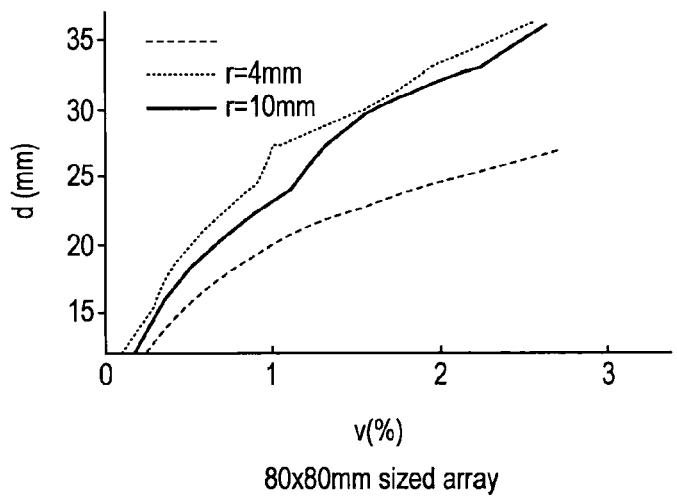
Figure 7D:
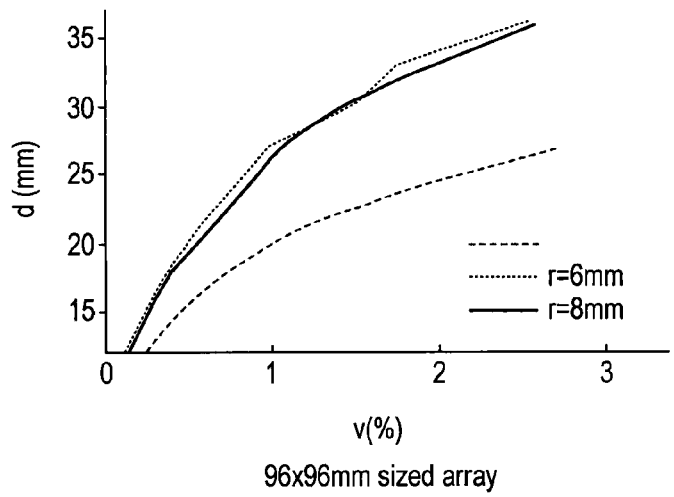
Figure 7E:
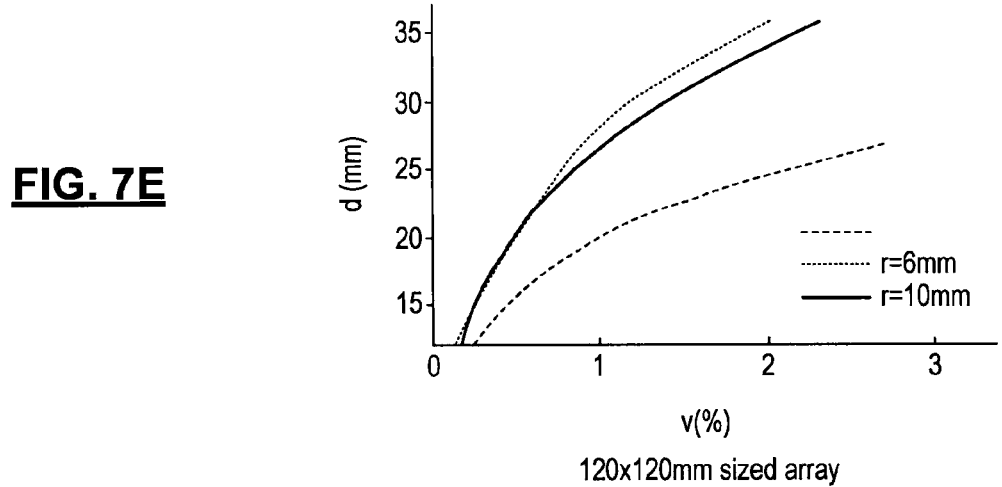
Figure 7F:
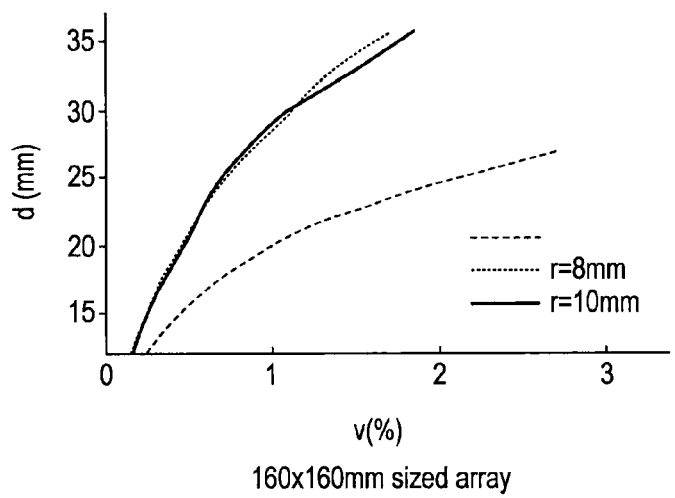
Figure 8A:
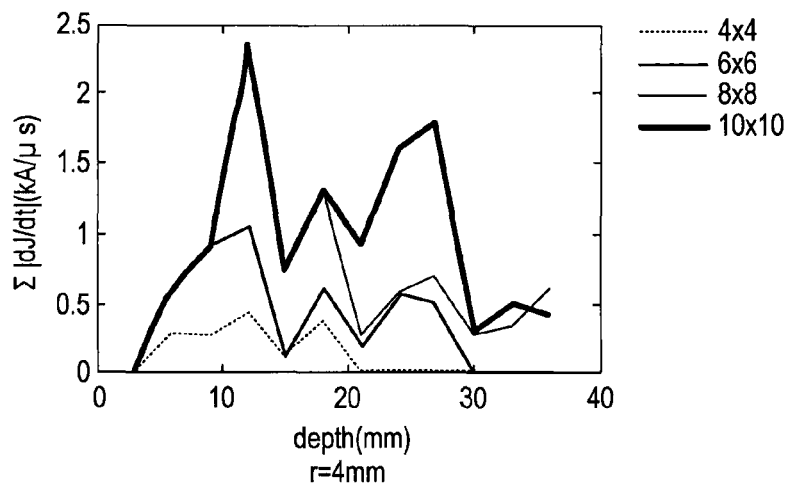
FIGS. 8A-8F are graphs illustrating the norm of current for each of the coil arrays.
Figure 8B:
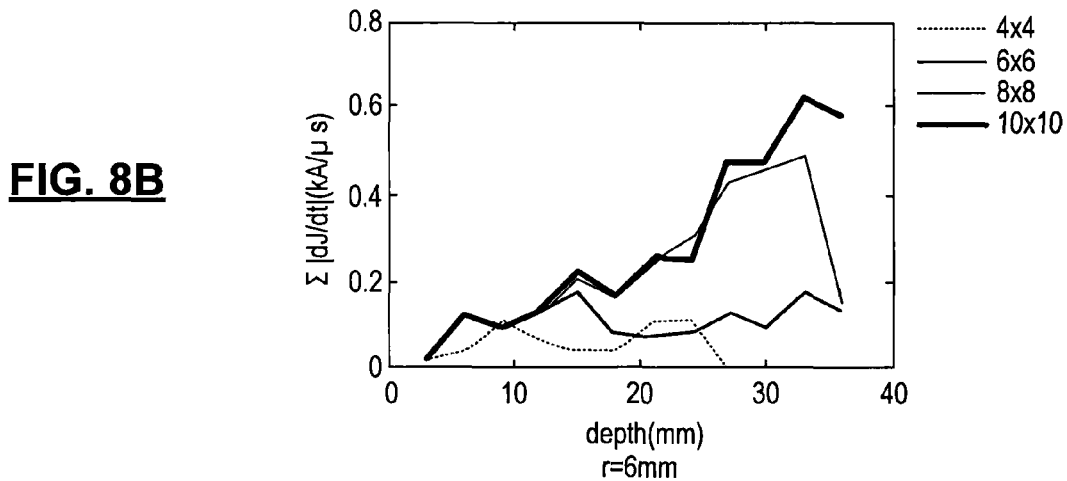
Figure 8C:
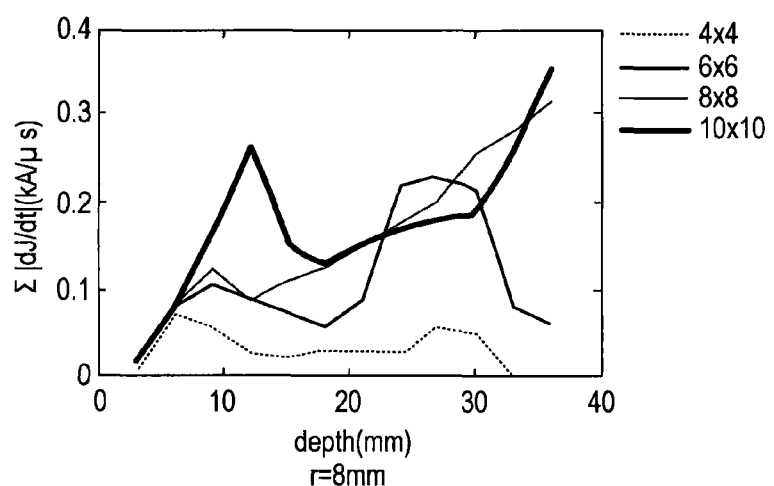
Figure 8D:
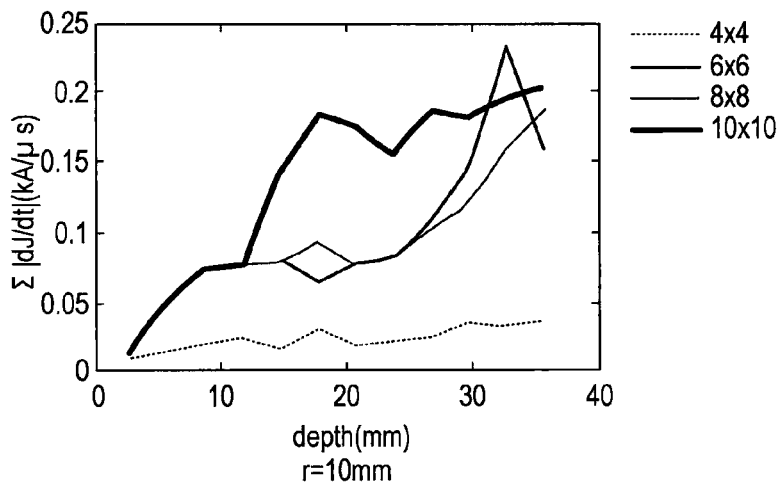
Figure 8E:
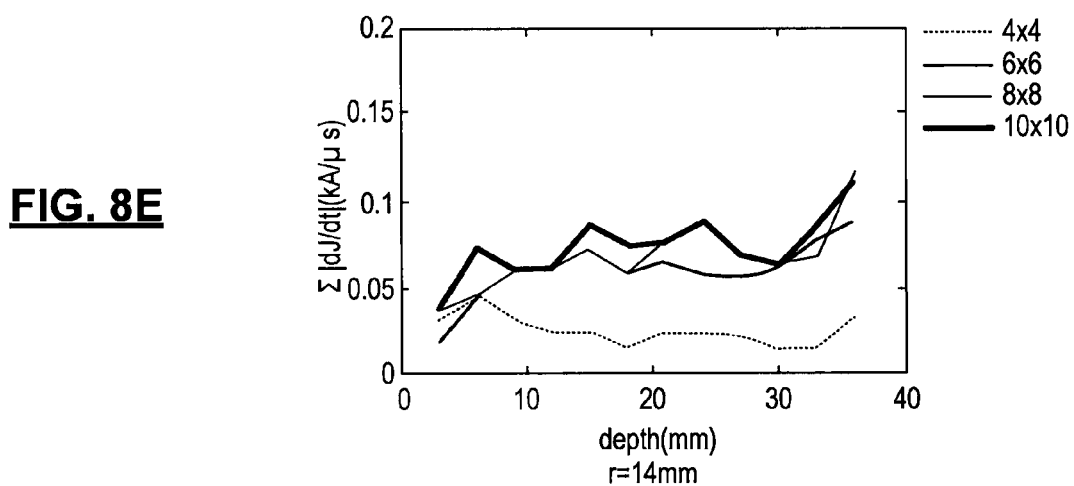
Figure 8F:
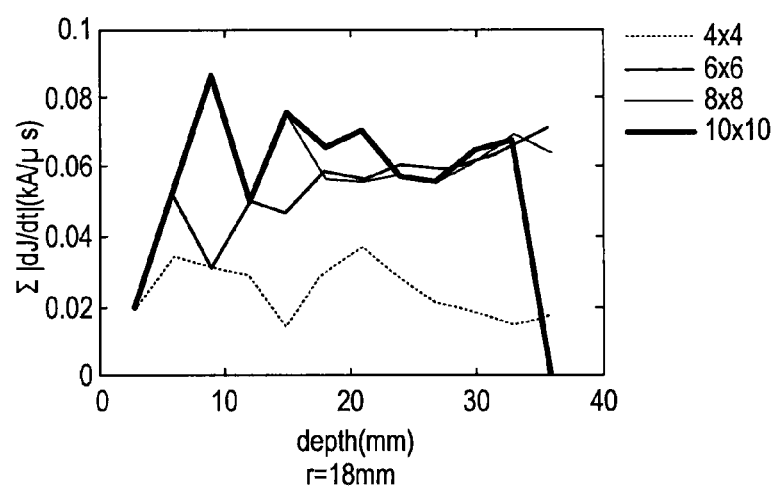

FIGS. 6 and 7 show the pareto optimal results for each of the arrays when compared to the best of the reference coils. Using multiple channels is superior to a single channel design for all cases that were tested. The electric fields generated by both the optimal figure-8 coil and the optimally driven 10×10 array composed of coils each with r=10 mm to target a depth of 24 mm into the head were plotted. The coil array excites a narrower region in both the sagittal and the coronal planes. In fact, for this case, the excited volume by the coil array is three times smaller than that of figure-8 coil. When comparing the individual arrays there are two main drivers for the improvement of the coils: the total size of the array, and the radius of each individual coil. A larger array is able to always reach deeper into the head than a smaller array, and if two arrays are of the same size, the one with the smaller coils dominates the one with larger coils. In FIGS. 6A-6F, the number of elements is changed, while maintaining the same size for the loops. Increasing the number of elements beyond 6×6 only marginally improves the focality of the coils; most of the gains from using more coils are seen by an increase in penetration of the fields. Thus, array size seems to be a primary driver of penetration. In FIGS. 7A-7F, each subplot contains pareto d-v tradeoffs for arrays of with identical size but composed of different sized loops. In all cases, using smaller loops results in a superior design than the ones where larger loops are used. Note that the actual gains from using smaller loops are marginal and for implementation the array with larger loops is more advantageous.

FIGS. 8A-8F illustrates plots with curves of the depth vs. L1 norm of the current for each of the array topology, within each plot the number of elements is varied while and the size of the individual coils are kept constant. For each depth the current increases by a factor between 1-10.24 when going from 16 elements to 100 and adding more coil elements lowers the total average current each element will support. No variation is seen in the magnitude of the currents between the currents of each individually sized arrays and thus increasing the number of elements by enlarge does not change the norms of the currents.

Figure 9A:
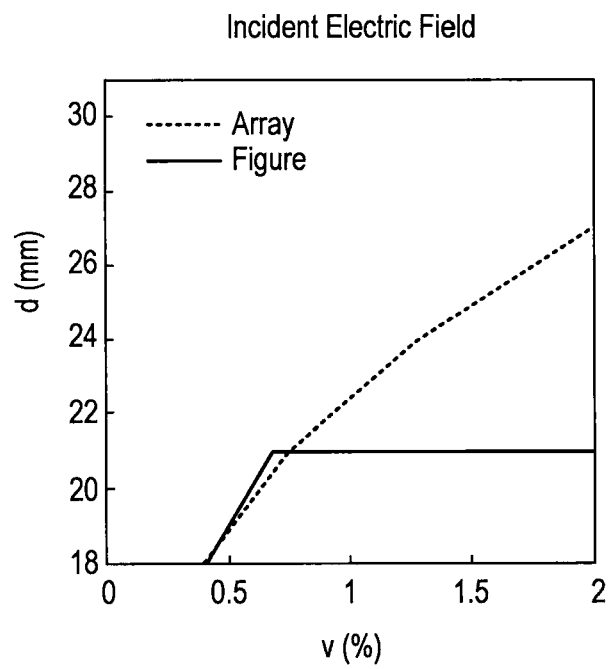
FIGS. 9A and 9B are graphs depicting an incident and total electric field, respectively, extracted from an MRI model of the head.
Figure 9B:
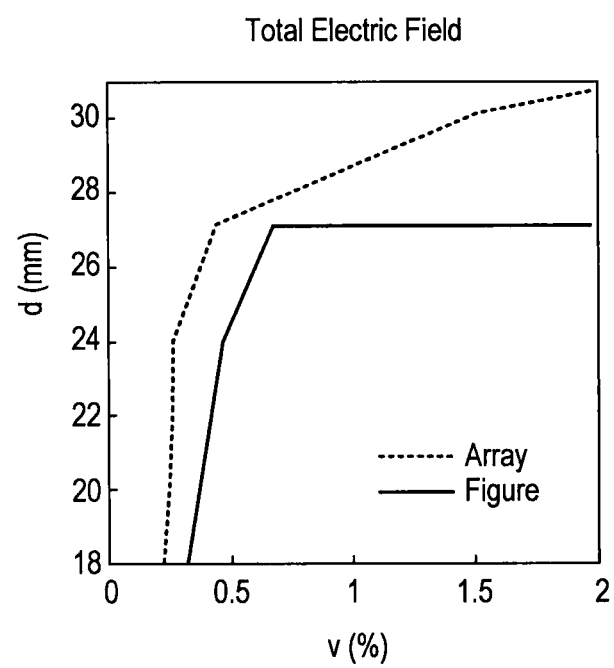

Additionally, the electric fields generated inside a more realistic MRI derived head model were calculated by the optimal array and conventional coil configurations for each depth to see if the results are valid in a more realistic scenario. A column placed directly over and normal to the region of the motor cortex responsible for hand movement was targeted—this location is of importance in TMS applications for depression. In FIG. 9A, the pareto front extracted from the incident field is plotted; whereas, in FIG. 9B, the one extracted from the total field is plotted. The head significantly changes both pareto fronts. While the optimized arrays still perform better than the conventional TMS coils, the gains are greatly reduced by secondary fields generated inside the head. This means that fields induced by charges induced on tissue interfaces can significantly affect the activated volume.

The computer-assisted techniques for designing the TMS apparatus described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-assisted method for constructing an apparatus for transcranial magnetic stimulation, comprising:
    modeling an apparatus for transcranial magnetic stimulation as an array of coils that induce an electric field at a given distance, each coil configured to receive a respective driving current;
    formulating a set of designs for the apparatus, each design is represented by a vector such that each element of the vector store a value of current driving a respective coil in the array of coils;
    iteratively applying a genetic algorithm to the set of designs by determining the electric field generated by each coil in the array of coils individually, calculating a total electric field induced by the array of coils from combining the individual electric fields from each of the coils in the array of coils, and evaluating each design according to a cost function that minimizes volume excited by the electric field at the given distance, thereby yielding an optimal design for the apparatus; and
    constructing the apparatus for transcranial magnetic stimulation based on the optimal design for the apparatus, wherein the apparatus for transcranial magnetic stimulation is configured to receive a driving current from a single source of current and has an array of coils electrically connected in series to each other, each coil being wound in a circle and a diameter of the circle is different amongst the coils in the array of coils.

2. The method of claim 1 wherein applying the genetic algorithm further comprises selecting parents from the set of designs using a roulette wheel selection procedure.

3. A computer-assisted method for constructing an apparatus for transcranial magnetic stimulation, comprising:
    modeling an apparatus for transcranial magnetic stimulation as an array of coils that induce an electric field at a given distance, each coil configured to receive a respective driving current;
    formulating a set of designs for the apparatus, each design is represented by a vector such that each element of the vector store a value of current driving a respective coil in the array of coils;
    iteratively applying a genetic algorithm to the set of designs by selecting parents from the set of designs using a roulette wheel selection procedure and applying a crossover operator and a mutation operator to the selected parents, thereby yielding an optimal design for the apparatus; and
    constructing the apparatus for transcranial magnetic stimulation based on the optimal design for the apparatus, wherein the apparatus for transcranial magnetic stimulation includes the array of coils electrically connected in series to each other and configured to receive a driving current from a single source of current.

4. The method of claim 3 wherein applying the genetic algorithm further comprises evaluating each design according to a cost function that minimizes volume excited by the electric field at the given distance.

5. The method of claim 4 wherein evaluating each design further comprises determining the electric field generated by each coil individually and calculating a total electric field induced by the array of coils from combining the individual electric fields from each of the coils in the array of coils.

6. A computer-assisted method for constructing an apparatus for transcranial magnetic stimulation, comprising:
    modeling an apparatus for transcranial magnetic stimulation as an array of coils that induce an electric field at a given distance, each coil configured to receive a respective driving current;
    formulating a set of designs for the apparatus, each design is represented by a vector such that each element of the vector store a value of current driving a respective coil in the array of coils;
    iteratively applying a genetic algorithm to the set of designs, thereby yielding an optimal design for the apparatus; and
    constructing the apparatus for transcranial magnetic stimulation in accordance with the optimal design for the apparatus, wherein the apparatus for transcranial magnetic stimulation has an array of coils electrically connected in series to each other and configured to receive a driving current from a single source of current, such that each coil in the array of coils is configured to mimic the magnetic dipole moment of a corresponding coil in the optimal design for the apparatus.

7. The method of claim 6 wherein applying the genetic algorithm further comprises evaluating each design according to a cost function that minimizes volume excited by the electric field at the given distance.

8. The method of claim 7 wherein evaluating each design further comprises determining the electric field generated by each coil individually and calculating a total electric field induced by the array of coils from combining the individual electric fields from each of the coils in the array of coils.

9. The method of claim 8 wherein applying the genetic algorithm further comprises selecting parents from the set of designs using a roulette wheel selection procedure.

* * * * *